(12) United States Patent
Lee et al.

(10) Patent No.: US 11,342,963 B2
(45) Date of Patent: May 24, 2022

(54) DEVICE AND METHOD FOR LOW-POWER BIDIRECTIONAL WIRELESS DATA TELEMETRY

(71) Applicant: Korea University Research and Business Foundation, Seoul (KR)

(72) Inventors: Hyung-Min Lee, Seoul (KR); Minjae Kim, Suwon-si (KR)

(73) Assignee: Korea University Research and Business Foundation, Seoul (KR)

( * ) Notice: Subject to any disclaimer, the term of this patent is extended or adjusted under 35 U.S.C. 154(b) by 71 days.

(21) Appl. No.: 17/006,991

(22) Filed: Aug. 31, 2020

(65) Prior Publication Data

US 2021/0111762 A1 Apr. 15, 2021

(30) Foreign Application Priority Data

Oct. 10, 2019 (KR) .................. 10-2019-0125611

(51) Int. Cl.
*H02J 50/12* (2016.01)
*H02J 50/80* (2016.01)
*H04B 5/00* (2006.01)
*A61N 1/372* (2006.01)
*A61N 1/378* (2006.01)

(52) U.S. Cl.
CPC ............ *H04B 5/0081* (2013.01); *H02J 50/12* (2016.02); *H02J 50/80* (2016.02); *H04B 5/0037* (2013.01); *A61N 1/378* (2013.01); *A61N 1/37211* (2013.01)

(58) Field of Classification Search
CPC ..... A61N 1/37211; A61N 1/378; H02J 50/10; H02J 50/12; H02J 50/80; H04B 5/0037; H04B 5/0075; H04B 5/0081

USPC ........................................................ 455/41.1
See application file for complete search history.

(56) References Cited

U.S. PATENT DOCUMENTS

| 9,795,794 | B2 | 10/2017 | Baumgartner et al. |
| 9,839,788 | B2 | 12/2017 | Dellamano et al. |
| 9,872,089 | B2 | 1/2018 | Ha et al. |
| 10,080,902 | B2 | 9/2018 | Dinsmoor et al. |
| 2010/0148723 | A1* | 6/2010 | Cook ............... G06K 19/07749 320/108 |

(Continued)

OTHER PUBLICATIONS

Lin, Yu-Po et al., "An Inductive Power and Data Telemetry Subsystem With Fast Transient Low Dropout Regulator for Biomedical Implants", *IEEE Transactions on Biomedical Circuits and Systems*, vol. 10, Issue 2, Apr. 2016 (pp. 435-444).

*Primary Examiner* — William Hernandez
(74) *Attorney, Agent, or Firm* — NSIP Law

(57) ABSTRACT

A device for low-power bidirectional wireless data telemetry includes: a coil unit configured to perform forward telemetry and back telemetry; a full-wave rectifier unit configured to convert an AC voltage into a DC voltage; a current modulator configured to change a magnetic field by altering a path of the AC current generated, when the back telemetry is performed; an energy storage configured to generate a reuse power using the AC current; and a LDO unit configured to generate a source voltage using the power output from the full-wave rectifier unit and the reuse power generated by the energy storage. Accordingly, since the back telemetry and the forward telemetry may be performed simultaneously and the wasted current is reused, the power required for back telemetry may be reduced.

9 Claims, 10 Drawing Sheets

(56) References Cited

U.S. PATENT DOCUMENTS

2011/0032044 A1  2/2011  Lee et al.
2021/0085119 A1* 3/2021  Zhang .................. A47J 27/004

* cited by examiner

FIG. 6

| Power(without LSK) | |
|---|---|
| Pin(rectifier) | 4.547mW |
| Pout(rectifier) | 3.74mW |
| PCE | 82% |
| Power(with LSK) | |
| Pin(rectifier) | 5.3mW |
| PSC | 0.7mW |
| Pout(rectifier) | 3.74mW |
| PCE | 69% |

DEVICE AND METHOD FOR LOW-POWER BIDIRECTIONAL WIRELESS DATA TELEMETRY

CROSS-REFERENCE TO RELATED APPLICATIONS

This application claims the benefit under 35 USC § 119(a) of Korean Patent Application No. 10-2019-0125611 filed on Oct. 10, 2019, in the Korean Intellectual Property Office, the entire disclosures of which are incorporated herein by reference for all purposes.

TECHNICAL FIELD

This disclosure relates to a device and method for efficient data telemetry with a wireless remote device, and more particularly, to a bidirectional data telemetry method in which a remote device transmits data to a central device by low-power wireless back telemetry and simultaneously receives forward telemetry data from the central device.

BACKGROUND ART

Implantable medical devices (IMD), which are implanted in the body, still have limitations in application to actual patients due to the limited lifespan and replacement cost of the internal battery. In addition, for stimulation or recording functions that directly inject current or voltage for therapeutic purposes, the IMD generally requires power of mW level.

In order to solve the power use problem of the implanted devices or wireless devices, many wireless power transmission techniques using an inductive link have been studied. FIG. 1 shows a wireless power technique using an inductive link.

Referring to FIG. 1, sending data from an external unit to an internal medical device (IMD) is called forward telemetry, and sending data from the internal medical device (IMD) to the external unit is called back telemetry.

These two data communication methods are important in that data information may be exchanged inside and outside the body. In particular, in the case of back telemetry, passive back telemetry that may be easily implemented in most applications is frequently used.

The passive back telemetry is operated by shorting a SC switch. If the SC switch is closed momentarily, the voltage at both ends of a L2 coil is shorted to instantaneously increase the current flowing through the L2 coil.

This current change changes the magnetic field formed between the coils and increases the voltage at both ends of the L1 coil to finally detect whether the SC switch is operating in a device outside the body. Through this, it is possible to implement back telemetry that transmits data to a device outside the body.

However, since the L2 coil is shorted whenever the back telemetry sends data through the SC switch, additional power is consumed. Also, during the back telemetry, since the voltage at both ends of the L2 coil is shorted, wireless power cannot be received from the device outside the body and forward telemetry data also cannot be received.

FIG. 2 shows a current wasted instantaneously in the direction from VIN1 to VIN2 when a secondary coil L2 is shorted by the SC signal during the back telemetry. Also, in a region where the SC switch is connected since the SC signal becomes high, wireless power cannot be received and forward telemetry cannot be performed.

Therefore, it is necessary to study a technique of designing a low-power back telemetry circuit that reduces the power required to send back telemetry data and a technology for receiving wireless telemetry and enabling forward telemetry even when back telemetry is performed.

The structure of the back telemetry frequently uses a load shift keying (LSK), which allows easy detection and simple circuit design. The LSK uses the SC switch described in FIG. 1 and is called load modulation or load shift keying because its load impedance is changed whenever the SC switch is connected.

If the back telemetry of the LSK method is performed, power consumption is caused by the current wasted whenever the back telemetry is performed, and also power is not received during the back telemetry, thereby decreasing the amount of wireless power transmitted to a wireless device.

Among the prior literatures, Non-patent Literature 1 ("Wireless power transfer with automatic feedback control of load resistance transformation", IEEE Trans. Power Electron (2016)) discloses a method of increasing the efficiency of back telemetry by preventing a shunt current flowing to an output resistor of a rectifier circuit that converts a wireless AC voltage into a DC voltage. However, there is a limitation that a wasted current still flows to the SC switch located in front of the rectifier and eventually power is still consumed whenever back telemetry is performed.

In addition, when back telemetry is performed using the LSK method, if the L2 coil is short-circuited, the voltage at both ends of the L2 coil drops to 0, and there is a disadvantage that forward telemetry data cannot be received during this period. This shows that back telemetry and forward telemetry must be performed in separate regions in a device where bidirectional data communication between the inside and outside of the body is important, such as neural recording.

For example, as in the existing method of FIG. 3, bidirectional communication may be enabled by setting signal timing differently for back telemetry and forward telemetry. However, in order to match the operation timing of the back telemetry and the forward telemetry, there is a disadvantage that the system design becomes complicated since both devices must use the same reference clock.

Among the prior literatures, Patent Literature 1 (KR 9872089 B1) discloses a circuit design technique for shortening the L2 coil using a data-synchronized cyclic on-off keying (COOK) method for back telemetry and implementing back telemetry with a low power by transmitting data through an inductive link while charge is preserved through the L2 coil. However, there is a problem that power is consumed during back telemetry.

RELATED LITERATURES

Patent Literature (Patent Literature 1) U.S. Pat. No. 9,872,089 B

Non-Patent Literature (Non-patent Literature 1) "Wireless power transfer with automatic feedback control of load resistance transformation", IEEE Trans. Power Electron (2016)

DISCLOSURE

Technical Problem

Accordingly, the present disclosure is designed in consideration of the above, and the present disclosure is directed to providing a device for low-power bidirectional wireless data telemetry.

The present disclosure is also directed to providing a method for low-power bidirectional wireless data telemetry.

Technical Solution

In one general aspect, there is provided a device for low-power bidirectional wireless data telemetry, comprising: a coil unit configured to receive a wireless power through induced inductance with the external device and perform a forward telemetry for receiving data wirelessly from the external device and a back telemetry for transmitting data wirelessly to the external device by generating an AC current; a full-wave rectifier unit configured to convert an AC voltage generated in the coil unit into a DC voltage; a current modulator configured to change a magnetic field of the coil unit by altering a path of the AC current generated in the coil unit, when the back telemetry for transmitting data to the external device is performed; an energy storage configured to generate a reuse power using the AC current supplied by the current modulator; and a LDO (low dropout voltage) unit configured to generate a source voltage using the power output from the full-wave rectifier unit and the reuse power generated by the energy storage.

In an embodiment of the present disclosure, the current modulator may include: a first SC switch and a second SC switch respectively coupled to both ends of the coil unit to receive a back telemetry signal; a first comparator and a second comparator respectively configured to receive signals of the first SC switch and the second SC switch as an input signal; and a first switch and a second switch respectively formed at output terminals of the first comparator and the second comparator to give a path of the AC current of the coil unit.

In an embodiment of the present disclosure, the LDO unit may include: an analog LDO unit configured to generate an analog source voltage using the power output from the full-wave rectifier unit; and a dual-input LDO unit configured to generate a digital source voltage using the power output from the full-wave rectifier unit and the reuse power generated by the energy storage.

In an embodiment of the present disclosure, the dual-input LDO unit may include: a main LDO unit configured to generate a digital source voltage using the power output from the full-wave rectifier unit; and a sub LDO unit configured to generate a digital source voltage using the reuse power generated by the energy storage.

In an embodiment of the present disclosure, the sub LDO unit may include: a feedback loop configured to adjust a level of the reuse power; a pass transistor configured to transmit the reuse power; and a load resistor configured to generate a digital source voltage through the pass transistor.

In an embodiment of the present disclosure, the analog LDO unit may include: a boost converter configured to boost an output voltage of the current modulator; and an analog LDO unit configured to generate an analog source voltage using the output power of the boost converter.

In order to accomplish another object of the present disclosure, a method for low-power bidirectional wireless data telemetry according to an embodiment comprises: receiving a wireless power by generating an induced inductance with an external device through a coil unit; converting the AC voltage into a DC voltage; changing a magnetic field of the coil unit by pulling the AC current, when back telemetry for transmitting data to the external device is performed; generating a reuse power by using the AC current; and generating a source voltage by using the power generated from the DC voltage and the reuse power.

In an embodiment of the present disclosure, in the method for low-power bidirectional wireless data telemetry, while the back telemetry is being performed, forward telemetry for receiving data wirelessly from the external device may be performed simultaneously.

In an embodiment of the present disclosure, said generating of a source voltage by using the power generated from the DC voltage and the reuse power may include: generating an analog source voltage by using the power; and generating a digital source voltage by using the power and the reuse power.

In an embodiment of the present disclosure, said generating of a digital source voltage may include: generating a digital source voltage by using the power; and generating a digital source voltage by using the reuse power.

Advantageous Effects

According to the device and method for low-power bidirectional wireless data telemetry, there is proposed a circuit design technology capable of reusing a wasted current according to an SC signal when back telemetry is performed.

Accordingly, when back telemetry is performed, since forward telemetry may be performed simultaneously and the wasted current is reused, the power required for back telemetry may be reduced. In addition, since a wireless power may be received during back telemetry, it is possible to increase the amount of wireless power transmitted to the wireless device. These technologies may make a great contribution to securing techniques of various wireless devices such as bio industry and wireless charging.

DESCRIPTION OF DRAWINGS

FIG. 6 is a table in which the power efficiencies of wireless power receiving terminals of the conventional back telemetry of FIG. 4 and the back telemetry of FIG. 5 according to the present disclosure are compared.

BEST MODE

Figure 1:
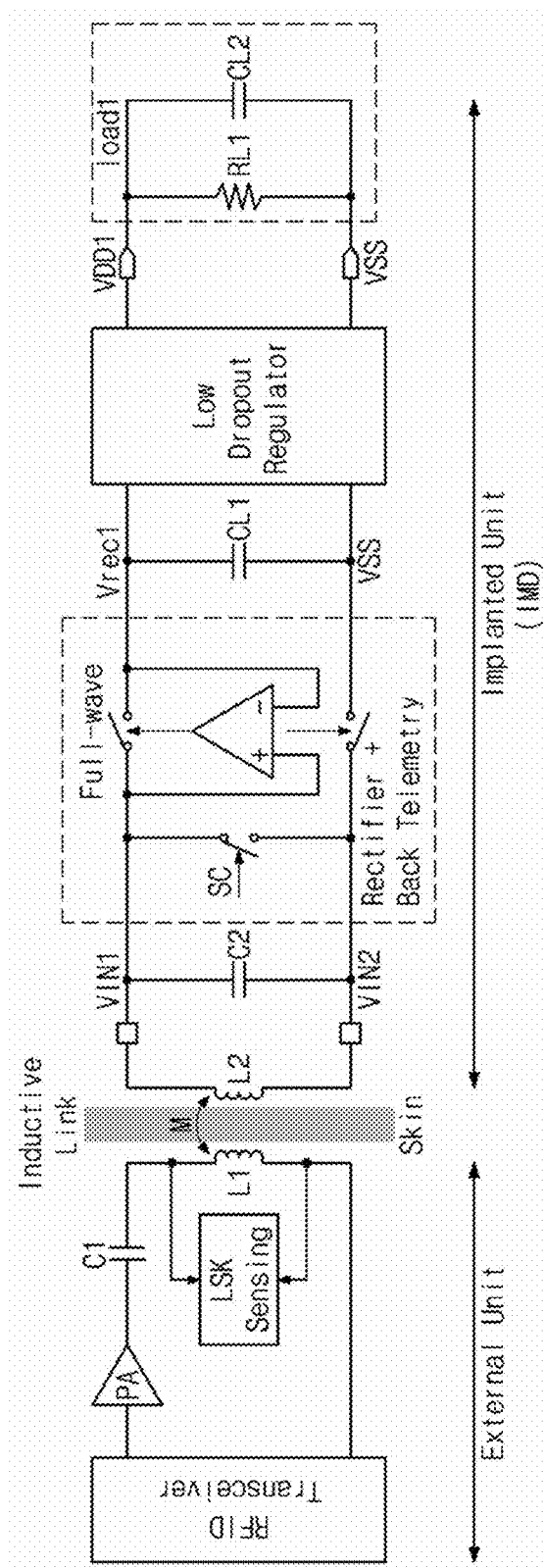
FIG. 1 is a circuit diagram showing a conventional wireless power technique using an inductive link of an IMD.
Figure 2:
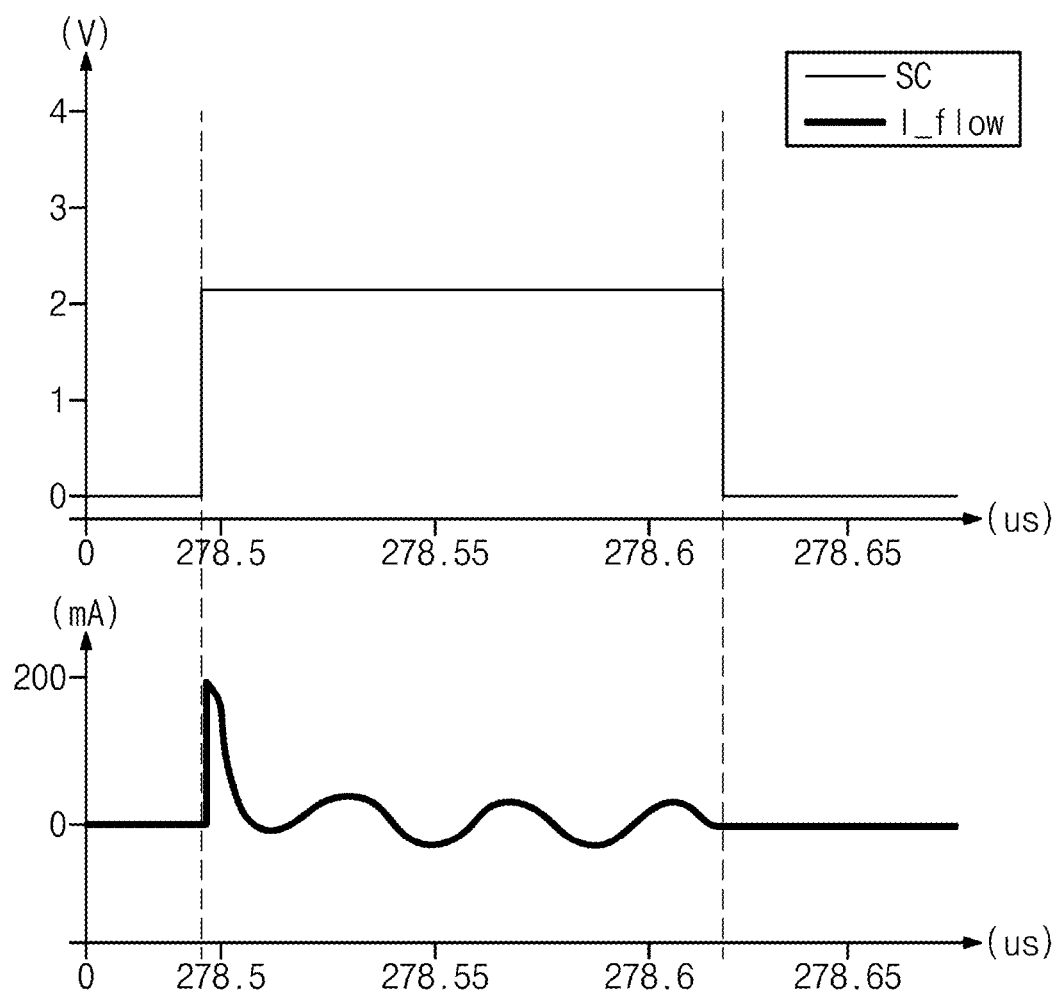
FIG. 2 is a graph showing a current wasted in a secondary coil using a short coil (SC) data signal of FIG. 1.
Figure 3:
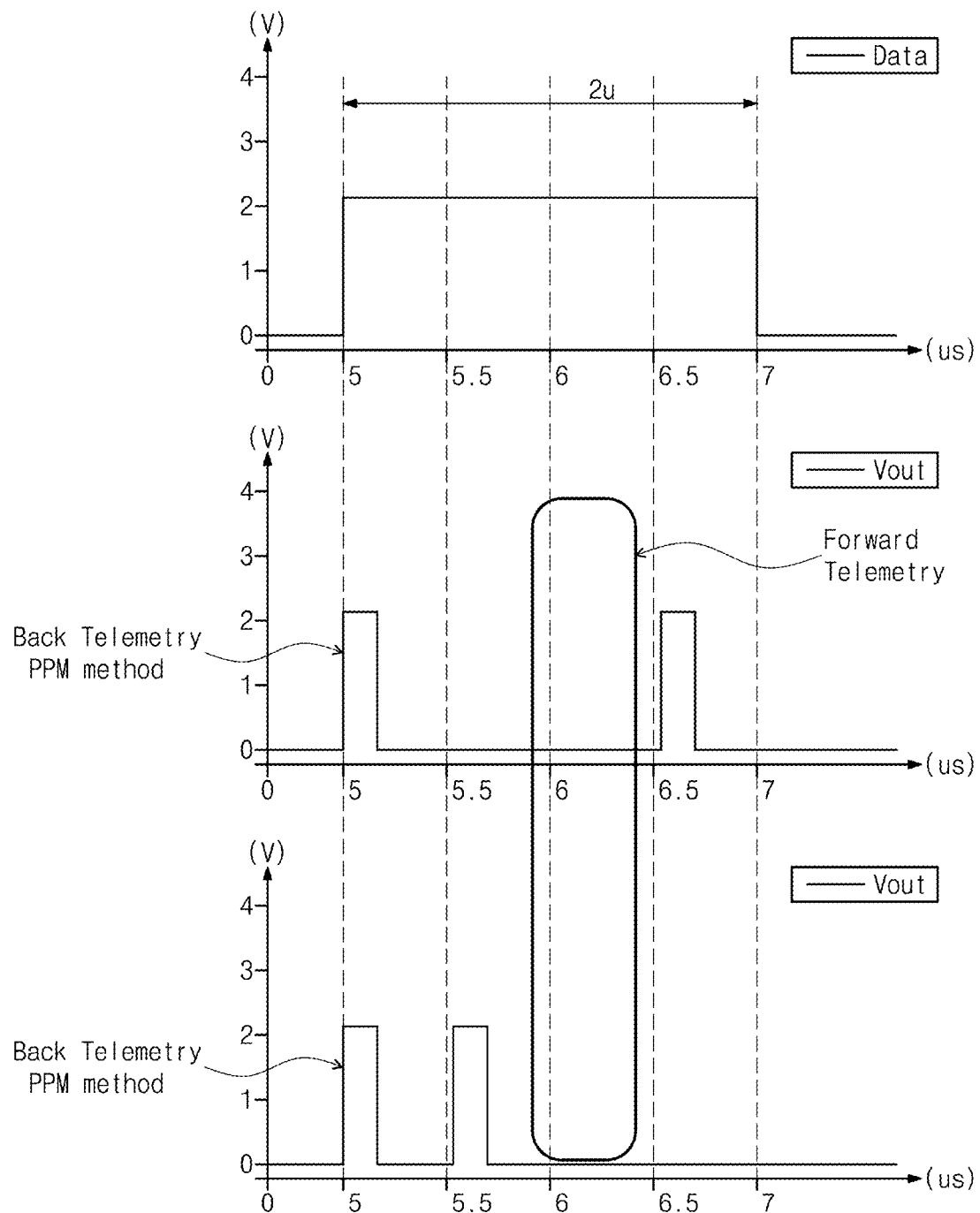
FIG. 3 is a pulse diagram showing conventional bidirectional data communication.

The present disclosure will be described in detail with reference to the accompanying drawings which illustrate, by way of example, specific embodiments in which the present disclosure may be implemented. These embodiments are described in sufficient detail to enable those skilled in the art to implement the present disclosure. It should be understood that various embodiments of the present disclosure are different from each other but need not be mutually exclusive. For example, specific features, structures and characteristics described herein may be implemented in other embodiments without departing from the scope of the present disclosure in connection with one embodiment. It should also be understood that the position or arrangement of individual components in each embodiment may be varied without departing from the scope of the present disclosure. Therefore, the following detailed description is not taken to limit the present disclosure, and the scope of the present disclosure is limited only by the appended claims, along with the full scope of equivalents to which such claims are entitled. In the drawings, like reference signs refer to the same or similar functions throughout several aspects.

Hereinafter, preferred embodiments of the present disclosure will be described in more detail with reference to the drawings.

Figure 5:
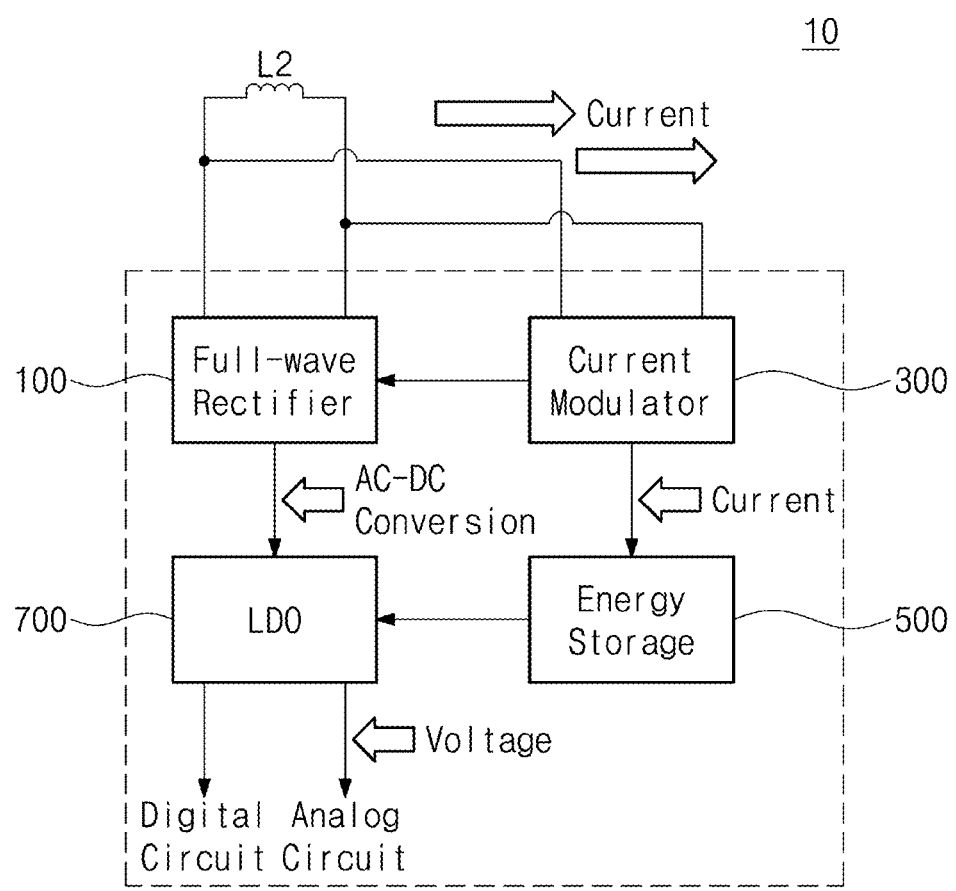
FIG. 5 is a diagram showing a back telemetry according to the present disclosure.
Figure 7:
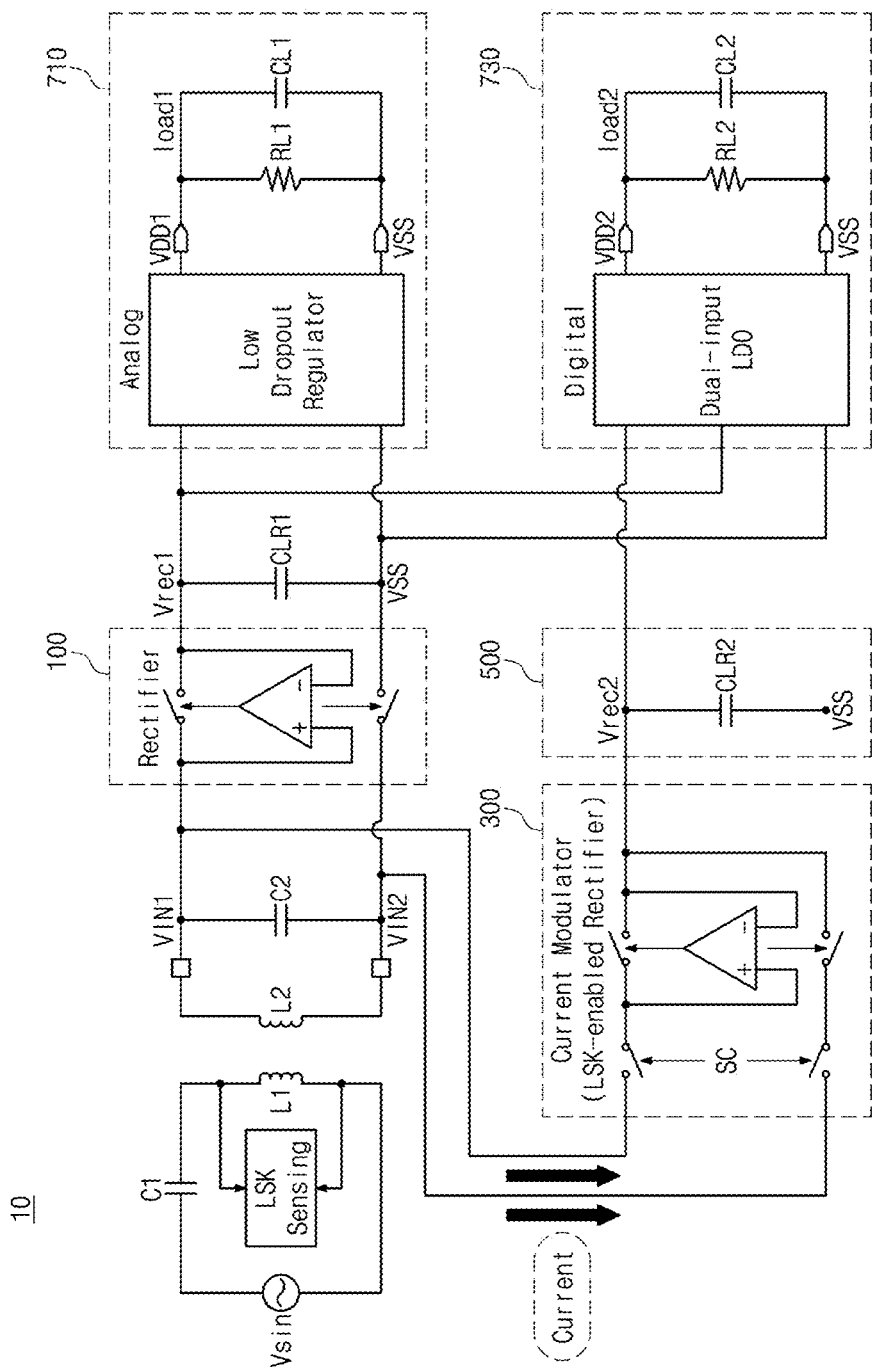
FIG. 7 is a block diagram showing a low-power bidirectional wireless data telemetry according to an embodiment of the present disclosure.

FIG. 5 is a diagram showing a back telemetry according to the present disclosure. FIG. 7 is a block diagram showing a low-power bidirectional wireless data telemetry according to an embodiment of the present disclosure.

Figure 4:
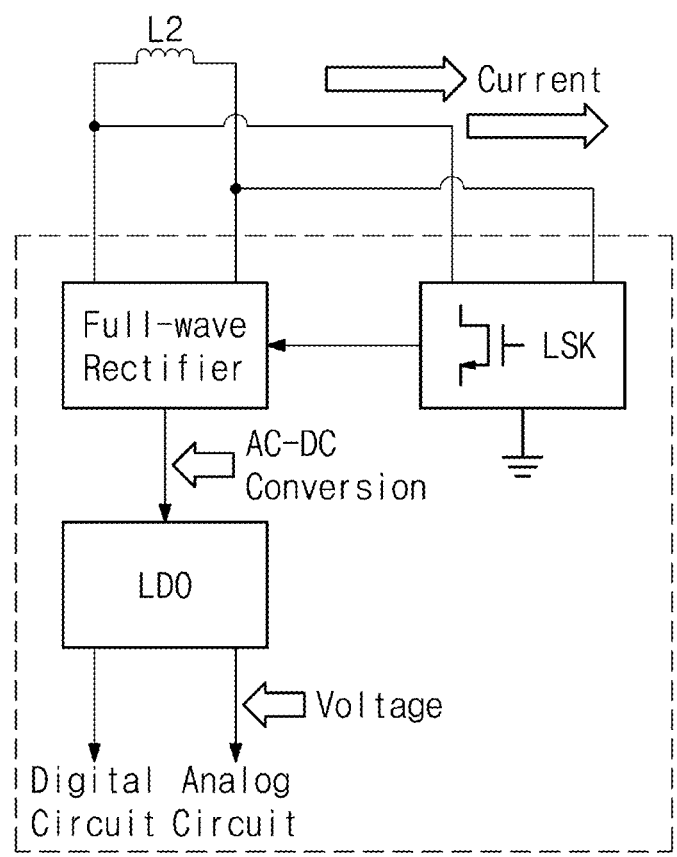
FIG. 4 is a diagram showing a conventional back telemetry.

The basic principle of back telemetry is to induce a voltage change on a L1 coil of an external device by instantaneously changing a current flowing through a L2 coil. FIG. 4 is a diagram showing a conventional back telemetry for comparison with the back telemetry of the present disclosure.

Referring to FIG. 4, the conventional back telemetry includes a rectifier for converting an AC voltage into a DC voltage and a low dropout regulator (LDO) for supplying a fixed source voltage, and performs the back telemetry by using a load shift keying (LSK) method.

In contrast, the back telemetry method proposed in the present disclosure additionally uses a circuit serving as a current modulator 300, instead of the existing LSK circuit (SC switch).

When sending back telemetry data, the current modulator 300 instantaneously pulls a current to change a magnetic field between the coils. Accordingly, the voltage at both ends of the L1 coil of the external device is increased, and the increased voltage may be detected in the external device. In addition, the pulled current is stored again through a circuit serving as an energy storage 500 and reused as a source voltage for the system.

Through this, it is possible to dramatically reduce the power required whenever performing back telemetry by reusing the wasted current during back telemetry. Also, during the back telemetry of the proposed method of the present disclosure, the L2 coil is not short-circuited, so the voltage at both ends of the coil does not become completely 0V.

Therefore, there is proposed a design technique that may still receive a power during back telemetry and detect forward telemetry data by using the fact that the voltage at both ends of the L2 coil does not become 0V.

Referring to FIGS. 5 and 7, a device 10 for low-power bidirectional wireless data telemetry device according to the present disclosure (hereinafter, referred to as a device) includes a coil unit L2, a full-wave rectifier unit 100, a current modulator 300, an energy storage 500 and a LDO unit 700.

The coil unit L2 receives a wireless power through induced inductance with the external device (L1 coil) and performs a forward telemetry for receiving data wirelessly from the external device and a back telemetry for generating an AC current and transmitting data wirelessly to the external device.

The full-wave rectifier unit 100 converts the AC voltage generated at the coil unit L2 into a DC voltage. A capacitor CLR1 for storing charge is formed at both ends of the full-wave rectifier unit 100 to output a voltage (Vrec1).

When performing the back telemetry of sending data to the external device, the current modulator 300 changes the path of the AC current generated in the coil unit L2 to alter the magnetic field of the coil unit L2, thereby inducing the change of voltage at the coil of the external device to transmit data.

The energy storage 500 generates a reuse power using the AC current supplied by the current modulator 300, and the LDO unit 700 generates a source voltage using the power output from the full-wave rectifier unit 100 and the reuse power generated from the energy storage 500.

The LDO unit 700 may include an analog LDO unit 710 for generating an analog source voltage and a digital LDO unit 730 for generating a digital source voltage.

Software (application) for performing low-power bidirectional wireless data telemetry may installed and executed in the device 10 of the present disclosure, and the coil unit L2, the full-wave rectifier unit 100, the current modulator 300, the energy storage 500 and the LDO unit 700 may be controlled by the software for performing the low-power bidirectional wireless data telemetry executed in the device 10.

The device 10 may be a separate terminal or some modules of the terminal. For example, the device 10 may be applied to implantable medical devices (IMD), implantable devices or wireless devices, or may form some modules. Further, the external device may be an external device out of the body, which is separate from the device 10.

In addition, the coil unit L2, the full-wave rectifier unit 100, the current modulator 300, the energy storage 500 and the LDO unit 700 may be formed as an integrated module, or may be made of one or more modules. However, on the contrary, these components may also be configured as separate modules.

As described above, it is obvious that power is consumed if current is wasted during back telemetry. FIG. 6 shows input power and power efficiency required when the LSK of the present disclosure is not used and when the conventional LSK is used to generate the same rectifier output power.

In the back telemetry operation section, Pout (rectifier) is the same, but the Pin increases. Here them, it may be seen that the power consumed when the voltage at both ends of L2 is shorted by connecting the switch occupies as much as 0.7 mW. Therefore, if the LSK is used, due to additional power consumption, input power is required more, and overall power efficiency is lowered.

If the input power is limited such as in an implantable device or a wireless IoT device, it is difficult to make a desired output power. In addition, if the input power is increased, adverse effect may be applied to the human body due to tissue absorption or the like of an implantable wireless bio circuit such as neural recording/stimulation IC.

Figure 8:
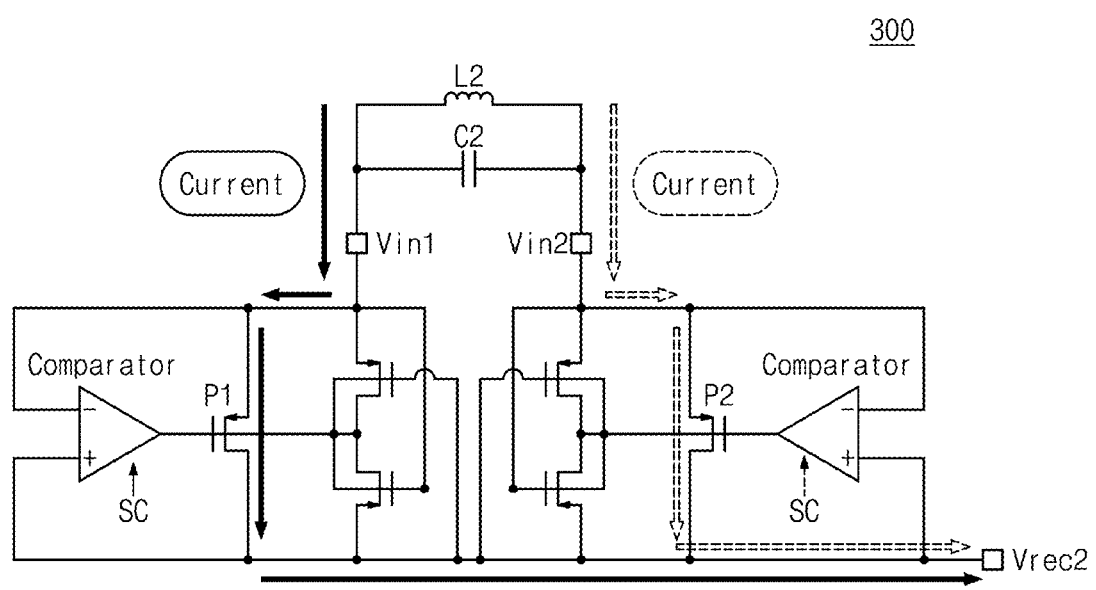
FIG. 8 is a circuit diagram showing an example of a current modulator of FIG. 7.

FIG. 8 shows a circuit structure of a current modulator 300 (LSK-enabled rectifier) that pulls a wasted current during back telemetry.

Referring to FIG. 8, the current modulator 300 may be configured by using a structure of a half-wave rectifier and adding a back telemetry signal SC switch to the comparator.

When the back telemetry does not work (SC switch=low), PMOS switches P1, P2 are all turned off by the comparator, so no current flows. In the case of back telemetry, (SC switch=high) may be classified into two cases, namely (P1 ON, P2 OFF) and (P1 OFF, P2 ON).

In the first case (P1 ON, P2 OFF), current flows from VIN1 to Vrec2 (indicated by a solid arrow in FIG. 8). In the second case (P1 OFF, P2 ON), current flows from VIN2 to Vrec2 (indicated by a dotted arrow in FIG. 8).

Figure 9:
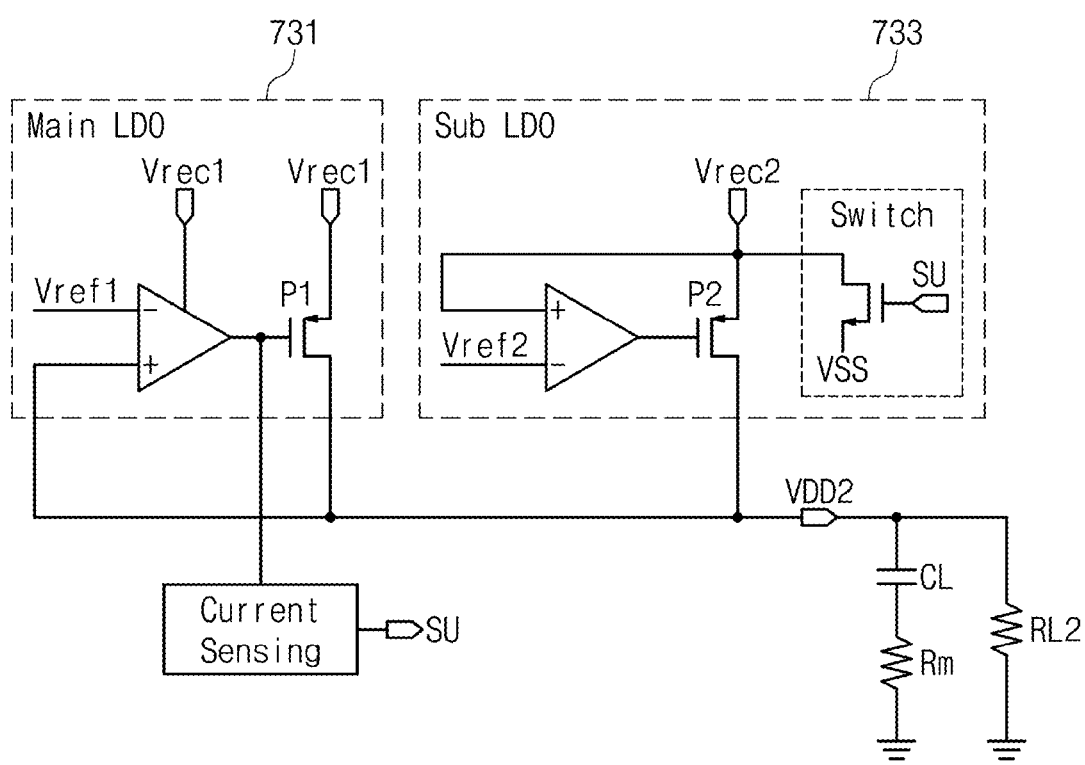
FIG. 9 is a circuit diagram showing an example of a dual-input LDO unit of FIG. 7.

FIG. 9 is a diagram showing a dual-input LDO designed to reuse the current consumed by back telemetry. The back telemetry system proposed in the present disclosure is configured by using the existing rectifier and the existing analog LDO and adding an LSK-enable rectifier that serves as the current modulator 300.

In addition, the dual-input LDO is configured by adding a sub LDO 733 using the reuse power (Vrec2) to a main LDO 731 using the existing power (Vrec1). The back telemetry technology proposed in the present disclosure instantly pulls the current through the current modulator 300 (LSK-enable rectifier) whenever transmitting data, and the current is charged to the capacitor CLR2.

The reused voltage (Vrec2) is adjusted to have the same level as Vref2 (e.g., 1.1V) by the feedback loop of the sub LDO 733, and this Vrec2 voltage is supplied to a load resistor RL2 of the dual-input LDO through a pass transistor P2 of the sub LDO 733 to generate a digital source voltage (VDD2).

Here, in general, the analog source voltage (VDD1) has a higher value than the digital source voltage (VDD2). In this embodiment, the analog source voltage (VDD1) and the digital source voltage (VDD2) are distinguished, but the present disclosure may also be applied to a system having one source voltage (e.g., using only the analog source voltage VDD1) by adding a boost converter circuit for raising voltage next to the current modulator 300.

Referring to FIG. 9, in order to generate the digital source voltage (VDD2), the dual-input LDO obtains power from the existing voltage (Vrec1) through the main LDO 731 and also obtains power from the reuse voltage (Vrec2) through the sub LDO 733.

In this structure, the power for generating the digital source voltage (VDD2) is firstly obtained through the reuse voltage (Vrec2), and if the power is insufficient, the power may be supplemented through the existing voltage (Vrec1). Therefore, it is possible to increase the power efficiency of the overall power conversion/supply system by reusing and supplying the power consumed during using back telemetry as the power required for generating the digital source voltage (VDD2).

If the back telemetry is performed as in the present disclosure, the voltage at both ends of the L2 coil does not completely become 0V. Due to this, power may be received during back telemetry, thereby not only increasing the amount of wireless power transmitted to a wireless device but also receiving forward telemetry data.

Figure 10:
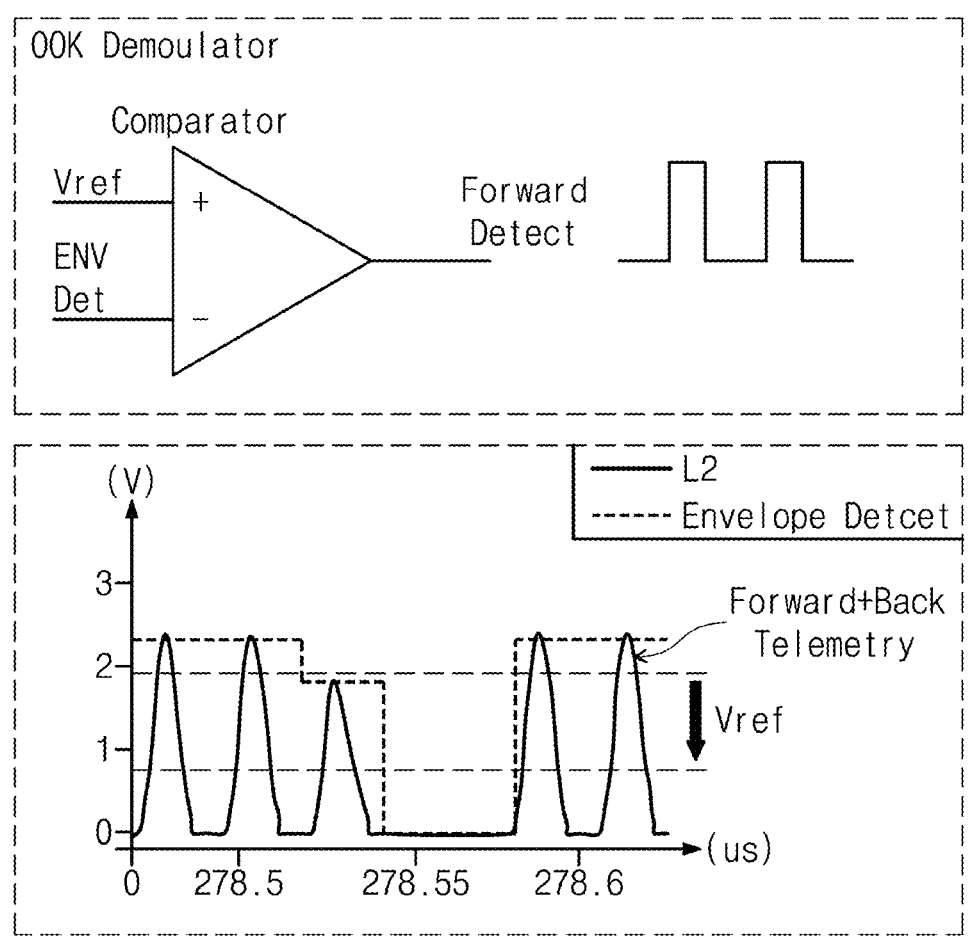
FIG. 10 is a diagram for illustrating a method for detecting data of the forward telemetry of FIG. 7.

FIG. 10 shows a demodulator design technique of forward telemetry proposed in the present disclosure and a method of detecting data of the forward telemetry, when back telemetry is being performed. Among various forward telemetry methods, the on-off keying (OOK) method, which may be easily implemented with low transmission error, is described as an example.

OOK is a method that does not send wireless power instantaneously while transmitting wireless power so that data are transmitted to be distinguished as 1 or 0. The OOK demodulator circuit classifies data by comparing a reference voltage (Vref) and an envelope voltage of the wireless power signal using a comparator.

If the envelope of the wireless power signal is greater than Vref (when the wireless power is received normally), the output of the comparator circuit is 0V. On the contrary, if the envelope of the wireless power signal is smaller than Vref (when the wireless power is arbitrarily disconnected), the output of the comparator circuit is sent to the source voltage (VDD).

The proposed OOK demodulator method uses the fact that the voltage at both ends of the L2 coil does not become 0V when LSK is performed using the LSK method proposed above. As shown in FIG. 10, the LSK method proposed in the present disclosure is to lower Vref of the OOK demodulator below 1V (which may vary depending on the system) by using the fact that the voltage at both ends of the L2 coil does not become 0V.

If so, forward telemetry data may be received using low Vref even when back telemetry data is being transmitted using the LSK.

The present disclosure proposes an LSK method that implements back telemetry by arbitrarily adjusting the current flowing from the coil using the current modulator 300.

In addition, by separately storing and reusing the current consumed when transmitting back telemetry data, the power efficiency of the overall system may be increased and the back telemetry may be performed at low power.

In addition, the current consumed when transmitting back telemetry data may be reused to generate the system source voltage, and the wireless power may still be received by using the fact that the voltage at both ends of the coil does not drop to 0V during the back telemetry. Accordingly, the forward telemetry data may be received simultaneously during back telemetry.

The method for low-power bidirectional wireless data telemetry as described above may be implemented in the form of an application or program commands executable by various computer components and be recorded on a computer-readable recording medium. The computer-readable recording medium may include program commands, data files, data structures or the like solely or in combination.

The program commands recorded on the computer-readable recording medium may be specially designed or configured for the present disclosure or known to and available by computer software engineers.

The computer-readable recording medium includes, for example, magnetic media such as a hard disk, a floppy disk and a magnetic tape, optical media such as CD-ROM and DVD, magneto-optical media such as a floptical disk, hardware devices such as ROM, RAM and a flash memory, specially configured to store and perform program commands, or the like.

The program commands include not only machine codes made by a complier but also high-level language codes executable by a computer by using an interpreter. The hardware device may be configured to operate as at least one software module to perform the operations of the present disclosure, or vice versa.

While the present disclosure has been described with reference to the embodiments, it will be understood by those skilled in the art that various changes and modifications can be made without departing from the scope of the present disclosure as set forth in the appended claims.

INDUSTRIAL APPLICABILITY

The method for low-power bidirectional wireless data telemetry proposed in the present disclosure may be applied not only to implantable medical devices, but also to commercial products such as wireless IoT devices and wireless charging devices that require wireless data transmission, and may especially be a key technology for the production of low-power, high-efficiency implantable devices that essentially use wireless power and data telemetry.

The low-power back telemetry and simultaneous forward telemetry technologies required for bidirectional communication with wireless devices may be applied to various products such as bio-industry, wireless IoT devices, and wireless chargers.

In Korea, companies such as Samsung and LG, which manufacture cell phones, are researching related wireless devices. In foreign countries, Medtronic of the United States is actively researching implantable devices that require wireless power and data telemetry. In addition, Biohax of Swedish is researching biotechnology for chip implants.

The invention claimed is:

1. A device for low-power bidirectional wireless data telemetry, comprising:
    a coil unit configured to receive a wireless power through induced inductance with an external device and perform a forward telemetry for receiving data wirelessly from the external device and a back telemetry for transmitting data wirelessly to the external device by generating an AC current;
    a full-wave rectifier unit configured to convert an AC voltage generated in the coil unit into a DC voltage;
    a current modulator configured to change a magnetic field of the coil unit by altering a path of the AC current generated in the coil unit, when the back telemetry for transmitting data to the external device is performed;
    an energy storage configured to generate a reuse power using the AC current supplied by the current modulator; and
    an LDO unit configured to generate a source voltage using a power output from the full-wave rectifier unit and the reuse power generated by the energy storage.

2. The device for low-power bidirectional wireless data telemetry according to claim 1,
    wherein the current modulator comprises:
    a first SC switch and a second SC switch respectively coupled to both ends of the coil unit to receive a back telemetry signal;
    a first comparator and a second comparator respectively configured to receive signals of the first SC switch and the second SC switch as an input signal; and
    a first switch and a second switch respectively formed at output terminals of the first comparator and the second comparator to give a path of the AC current of the coil unit.

3. The device for low-power bidirectional wireless data telemetry according to claim 1,
    wherein the LDO unit comprises:
    an analog LDO unit configured to generate an analog source voltage using the power output from the full-wave rectifier unit; and
    a dual-input LDO unit configured to generate a digital source voltage using the power output from the full-wave rectifier unit and the reuse power generated by the energy storage.

4. The device for low-power bidirectional wireless data telemetry according to claim 3,
    wherein the dual-input LDO unit comprises:
    a main LDO unit configured to generate a first digital source voltage using the power output from the full-wave rectifier unit; and
    a sub LDO unit configured to generate a second digital source voltage using the reuse power generated by the energy storage.

5. The device for low-power bidirectional wireless data telemetry according to claim 4,
    wherein the sub LDO unit comprises:
    a feedback loop configured to adjust a level of the reuse power;
    a pass transistor configured to transmit the reuse power; and
    a load resistor configured to generate the second digital source voltage through the pass transistor.

6. A method for low-power bidirectional wireless data telemetry, comprising:
    receiving a wireless power by generating an induced inductance with an external device through a coil unit;
    converting an AC voltage into a DC voltage;
    changing a magnetic field of the coil unit by pulling an AC current, when back telemetry for transmitting data to the external device is performed;
    generating a reuse power by using the AC current; and
    generating a source voltage by using a power generated from the DC voltage and the reuse power.

7. The method for low-power bidirectional wireless data telemetry according to claim 6,
    wherein while the back telemetry is being performed, forward telemetry for receiving data wirelessly from the external device is performed simultaneously.

8. The method for low-power bidirectional wireless data telemetry according to claim 6,
    wherein the generating the source voltage by using the power generated from the DC voltage and the reuse power comprises:
    generating an analog source voltage by using the power generated from the DC voltage; and
    generating a digital source voltage by using the power generated from the DC voltage and the reuse power.

9. The method for low-power bidirectional wireless data telemetry according to claim 8,
    wherein the generating the digital source voltage comprises:
    generating a first digital source voltage by using the power generated from the DC voltage; and
    generating a second digital source voltage by using the reuse power.

* * * * *